United States Patent [19]

Ono et al.

[11] Patent Number: 4,681,093

[45] Date of Patent: Jul. 21, 1987

[54] ENDOSCOPE

[75] Inventors: Kimizo Ono; Akira Nishimura, both of Osaka, Japan

[73] Assignee: Sumitomo Electric Industries, Ltd., Osaka, Japan

[21] Appl. No.: 560,104

[22] Filed: Dec. 12, 1983

[30] Foreign Application Priority Data

Dec. 13, 1982 [JP] Japan ............................. 57-188287[U]
Dec. 13, 1982 [JP] Japan ............................. 57-188288[U]
Jan. 19, 1983 [JP] Japan ................................ 58-7966[U]

[51] Int. Cl.⁴ ............................................... A61B 1/06
[52] U.S. Cl. ......................................................... 128/6
[58] Field of Search ..................... 128/4, 5, 6, 7, 8, 9

[56] References Cited

U.S. PATENT DOCUMENTS

| | | | |
|---|---|---|---|
| 3,417,745 | 12/1968 | Sheldon | 128/6 |
| 3,643,653 | 2/1972 | Takahashi et al. | 128/6 |
| 3,690,769 | 9/1972 | Mori | 128/6 X |
| 3,831,587 | 8/1974 | Boyd | 128/6 |
| 3,866,599 | 2/1975 | Johnson | 128/6 X |
| 4,284,081 | 8/1981 | Kasper et al. | 128/349 B |

FOREIGN PATENT DOCUMENTS

| | | |
|---|---|---|
| 2311807 | 3/1973 | Fed. Rep. of Germany . |
| 2848484 | 5/1979 | Fed. Rep. of Germany . |
| 3131652 | 2/1983 | Fed. Rep. of Germany . |
| 2278305 | 2/1976 | France . |
| PCT/US82/-01669 | 6/1983 | PCT Int'l Appl. . |
| PCT/US83/-00312 | 9/1983 | PCT Int'l Appl. . |

*Primary Examiner*—William H. Grieb
*Attorney, Agent, or Firm*—Cushman, Darby & Cushman

[57] ABSTRACT

An endoscope for image-observing or measuring an area filled with an opaque liquid is disclosed. The endoscope comprises an image fiber, a lens positioned at the leading end of the image fiber, a light guide arranged in parallel to the image fiber, a transparent fluid transport passage arranged in parallel to the image fiber and the light guide and having an outlet at the leading end thereof, a sheath enclosing the image fiber, lens, light guide and transparent fluid transport passage and a means for providing a field of vision at the leading end of the endoscope by a transparent fluid from the outlet of the transparent fluid transport passage. A means for stabilizing the field of vision formed by the field of vision providing means is provided on the leading end portion of the sheath.

17 Claims, 24 Drawing Figures

ENDOSCOPE

BACKGROUND OF THE INVENTION

This invention relates to an endoscope for image-observing or measuring an area filled with an opaque liquid. It has been known that an area filled with an opaque liquid such as a blood vessel or the internal wall of the heart of a living body may be observed by the use of an endoscope having a means for providing a field of vision by a transparent fluid.

FIG. 1 is a schematic view showing the principle of such an endoscope. In FIG. 1, 1 denotes a tube or catheter to be inserted into a living body, 2 denotes a blood vessel within the living body and 3 denotes an image fiber. Basically, the image fiber 3 is inserted into the catheter 1 and a transparent fluid is passed through the catheter 1 and is flushed into an observation area within the living body whereby the internal conditions of the body can be observed through the image fiber.

FIG. 2 shows one example of the leading end portion of the conventional endoscope provided with a transparent fluid flush means as a means for providing a field of vision. In FIG. 2, 3 denotes an image fiber for transmitting an image from the observation area to an optical system or measuring system not shown, 4 denotes a light guide for transmitting illumination light from a light source not shown to the observation area, 5 denotes a cylindrical lens set, 6 denotes a prism and 7, 8 denote advancing directions of transparent fluid and illumination light. The transparent material which may be a saline, is directly flushed from an outlet 9 into a blood vessel of a living body, for example, to dispel the blood from the observation area, whereby a transparent field of vision is formed in the blood vessel and the internal conditions of the blood vessel can be observed.

In this conventional endoscope shown in FIG. 2, however, since the field of vision must be maintained in a condition which is free of blood and is transparent by continuously excluding the flow of blood, a constant flow of a great amount of transparent fluid, usually an amount substantially corresponding to the amount of fluid flow within the blood vessel, must continuously be supplied to the area during the observation operation. The endoscope adapted to be inserted into a living body for observation of the living body preferably has as small an outer diameter as possible. However, in the endoscope shown in FIG. 2, in order to supply the transparent fluid in a great amount as mentioned hereinabove, the outer diameter of the endoscope becomes of necessity rather large. In addition, the supply of the transparent fluid in a great amount also requires the use of a specific electrically driven power cylinder to increase the supplying pressure of the transparent fluid.

In order to supplement such defects of the conventional endoscope above stated, another type of endoscope having a transparent balloon as a means for providing a field of vision at the leading end thereof has been proposed and has become conventionally known.

FIGS. 3 and 4 show longitudinally sectional and end elevational views, respectively, of a conventional endoscope 10a with a transparent balloon.

In these FIGS., 3a denotes an image fiber, 5a denotes a lens, 4a denotes light guides, 7a denotes a transparent fluid transport passage, 9a denotes a fluid outlet, 11 denotes a transparent balloon and 12 denotes a sheath. The transparent balloon 11 is secured to the sheath 12 by adhesive and binding means (not shown). When the internal wall of the heart of a living body is observed, for example, by inserting the endoscope into the living body, a transparent fluid such as $CO_2$ gas or a saline is passed through the transparent fluid transport passage 7a and discharged through the fluid outlet 9a to inflate the transparent balloon 11 at the leading end of the endoscope whereby a transparent field of vision is formed within the inflated transparent balloon 11.

FIG. 5 shows a conventional endoscope with a transparent balloon being used for the observation of the internal wall of the heart of a living body. The transparent balloon 11 inflated with the transparent fluid provides a transparent area 14 in contact with the heart's internal wall 13 between the endoscope and the heart's internal wall 13 whereby opaque blood 15 is excluded from the observation area to provide a field of vision for observation.

However, the above mentioned conventional endoscope with the transparent balloon has a small or insufficient support area for the large size of the transparent balloon 11 when inflated and, thus, has a low or insufficient support capacity for the balloon. For this reason, when the endoscope is inserted into a living body for the observation of the internal conditions of the living body, the inflated balloon 11 attached to the leading end of the endoscope sways at the joint between the endoscope body and balloon when subjected to a variation in the feed pressure of the transparent fluid and/or the reaction force from the living body tissue to be observed. Thus, the conventional endoscope with the transparent balloon has the disadvantage that the field of vision tends to be unstable during the observation operation. This sway of the balloon becomes greater when the thickness of balloon wall is made thinner in order to increase the transparency of the balloon.

FIGS. 6 and 7 show examples of the unstable conditions of the field of vision caused by the swaying of the inflated balloon at the joint between the endoscope body and balloon during the observation operation when subjected to outer force as shown by the arrows.

SUMMARY OF THE INVENTION

Therefore, the principal object of the present invention is to eliminate the disadvantages inherent in the conventional endoscopes for optically observing or measuring an observation area filled with an opaque liquid and to provide an improved endoscope which can provide a stable field of vision with a minimum amount of transparent fluid during the observation operation.

According to the present invention, an endoscope for image-observing or measuring an area filled with an opaque liquid comprises; an image fiber; a lens positioned at the leading end of said image fiber; a light guide arranged in parallel to said image fiber; a transparent fluid transport passage arranged in parallel to said image fiber and light guide and having an outlet at the leading end thereof; a sheath enclosing said image fiber, lens, light guide and transparent fluid transport passage; and a means for providing a field of vision at said leading end of said endoscope by the transparent fluid; and it is further characterized by a means for stabilizing said field of vision formed by the field of vision providing means which stabilizing means is provided on the leading end portion of said sheath.

In one preferred example of the invention, said field of vision providing means comprises a flush of said transparent fluid directly spouted out from said outlet of said transparent fluid transport passage into said opaque liquid and said stabilizing means comprises an expandable hood surrounding said lens, the outlet of said transparent fluid transport passage, the leading end of the light guide and the flush of the transparent fluid. By this arrangement, the field of vision is obtained stably at the observation area by a relatively small amount of transparent fluid and as a result, a transport passage of a relatively small diameter may be used for the transparent fluid, and thus the outer diameter of the endoscope can also be reduced and, at the same time, any specific electrically driven power cylinder for supplying the transparent fluid can be eliminated.

In another preferred example of the invention, said field of vision providing means comprises a transparent balloon provided at the leading end of said endoscope and is inflatable by said transparent fluid supplied from said passage and said stabilizing means comprises a balloon support formed by substantially cylindrical and resilient material and provided at the leading end portion of the endoscope encircling the portion which forms the joint between the balloon and the endoscope body so as to support the balloon joint portion when the balloon is inflated or, alternatively, a support balloon mounted on said sheath at the leading end portion of the endoscope behind said transparent balloon for supporting the backside of the same when said two balloons are inflated. By such arrangements also, the field of vision is obtained stably with a minimum amount of the transparent fluid being required.

Many other advantages, features and additional objects of the present invention will become apparent to persons skilled in the art upon making reference to the following description and the accompanying drawings which show preferred embodiments of the present invention by way of illustrative example.

BRIEF DESCRIPTION OF THE DRAWINGS

FIG. 20 is an explanative view of the endoscope with a transparent balloon according to the fourth embodiment of the present invention in which

FIG. 20 (c) shows an endoscope having separate fluid passages for the balloons according to the fourth embodiment of the invention, the balloons being shown in an inflated state; and FIG. 21 is a view showing one specific example of the fourth embodiment of the invention in which

PREFERRED EMBODIMENT OF THE INVENTION

Figure 8:
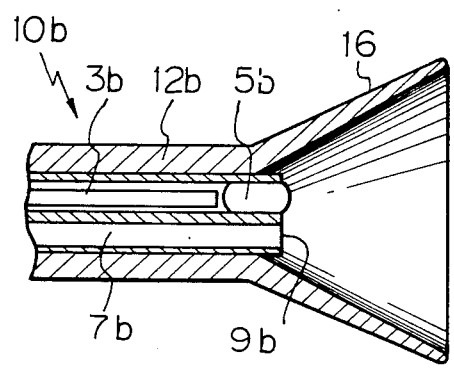
FIGS. 8 and 9 are longitudinally sectional and end elevational views, respectively, of the leading end portion of the endoscope according to the first embodiment of the present invention.
Figure 9:
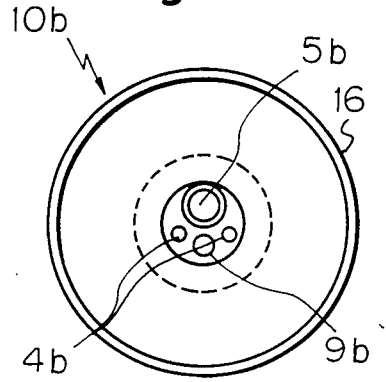

FIGS. 8 and 9 are cross-sectional and front elevational views of the leading end portion of the endoscope 10b of the first embodiment of the invention, respectively, In these FIGS., 3b denotes an image fiber, 4b denotes a light guide (shown in FIG. 9 only for clarity of presentation), 5b denotes a lens and 7b denotes a transparent fluid transport passage. These components are enclosed as a unit in a sheath 12b. The leading end of the transparent fluid transport passage 7b is formed with an outlet 9b. A resilient hood 16 is formed at the leading end of the sheath 12b as an integral extension of the sheath and encircles the leading ends of the passage 7b, lens 5b and light guide 4b.

Figure 10:
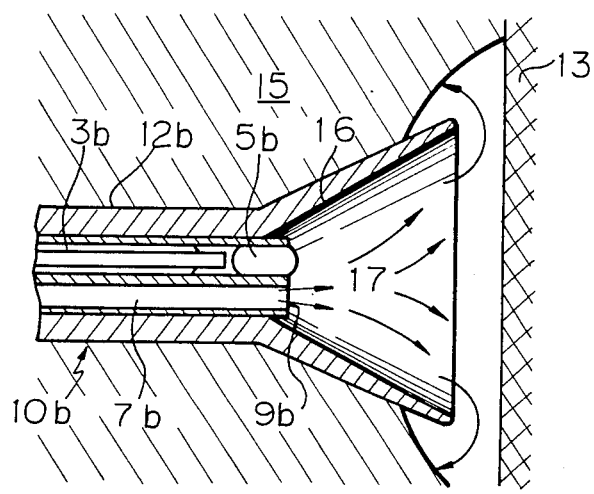
FIGS. 10 and 11 are views showing the operational modes of the endoscope of the first embodiment for observing a flat object such as the internal wall of the heart of a living body and a narrow field such as that in a blood vessel, respectively.
Figure 11:
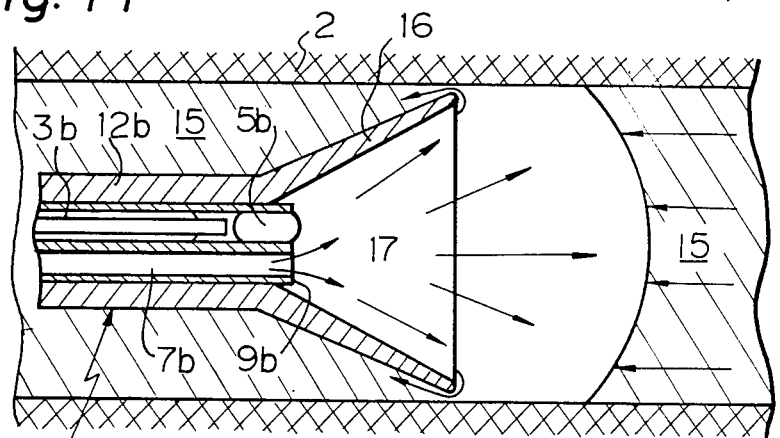

FIGS. 10 and 11 show the operation modes of the endoscope of the first embodiment for observing the internal conditions of a living body. FIG. 10 shows the operation mode of the endoscope for observing a flat object at an area for observation such as the internal wall 13 of the heart or the like, for example. FIG. 11 shows the operation mode of the endoscope for observing the internal conditions of a living body in the direction opposite to the flow direction of the blood 15 in relatively large blood vessel 2 such as the femoral artery, for example. The hood 16 holds the transparent fluid 17 such as a saline in a stable condition at a limited area to be observed excluding the blood therefrom to thereby provide the field of vision free of blood 15 with a small amount of transparent flow as a whole. That is, the observation is made possible through the transparent area defined by the hood adjacent to the light guide 4b and lens 5b.

Figure 12:
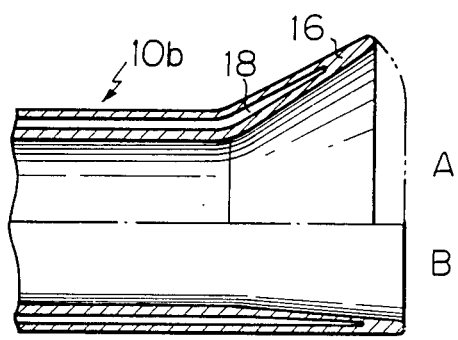
FIG. 12 is a sectional view showing the expansion and contraction of the resilient hood in the endoscope according to first embodiment of the present invention.

As shown in FIG. 12, the resilient hood 16 is expanded, as shown by reference character A, only when necessity arises, by inflating a balloon device 18 provided in the wall of the hood 18 and this hood may normally be kept in a deflated state as shown by reference character B. Thus, when the endoscope is inserted into the blood vessel, the hood 16 is contracted so that the endoscope can be easily inserted into the blood vessel and after the endoscope has been inserted into the blood vessel, the hood 16 is expanded whereby the observation area is easily formed.

With the above-mentioned construction and arrangement of the components of the endoscope of this first embodiment, a field of vision can be effectively formed in the observation area by the transparent fluid in a relatively small amount. As a result, the diameter of the transparent fluid transport passage can be reduced and thus, the outer diameter of the endoscope can also be reduced. Furthermore, as the reduced amount of the transparent fluid required a lower pressure for supplying the fluid, the endoscope can be operated by merely manipulating a manual cylinder for pushing the fluid (not shown) without the need of a specific electrically driven power cylinder.

Figure 1:
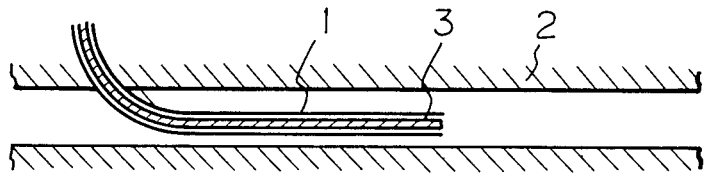
FIG. 1 is a schematic view for explaining the principle of an endoscope.
Figure 2:
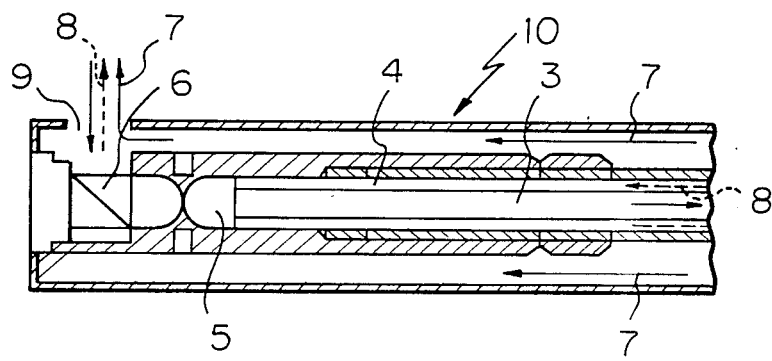
FIG. 2 is a view showing one example of the leading end portion of a conventional endoscope with a transparent fluid flush means.
Figure 3:
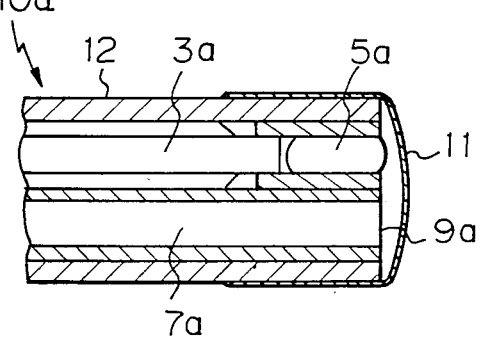
FIGS. 3 and 4 are longitudinally sectional and end elevational views, respectively, of a conventional endoscope with a transparent balloon.
Figure 4:
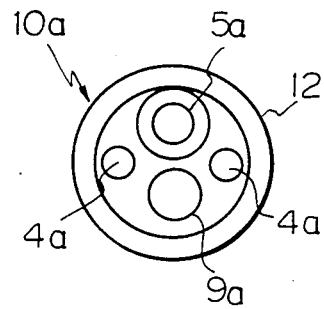
Figure 5:
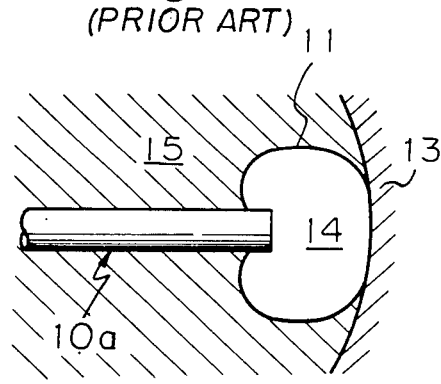
FIG. 5 is a view showing the observation operation of the internal wall of the heart of a living body by the conventional endoscope with a transparent balloon.
Figure 6:
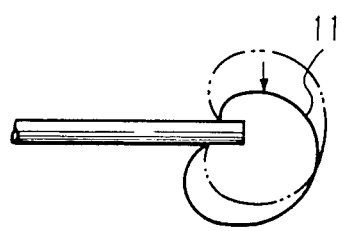
FIGS. 6 and 7 are views showing an unstable field of vision caused by the swaying of the transparent balloon at the joint thereof in the conventional endoscope.
Figure 7:
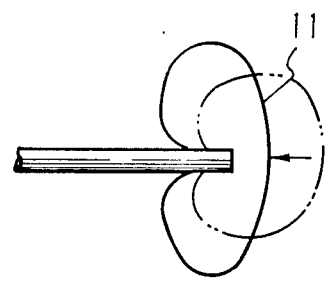
Figure 13:
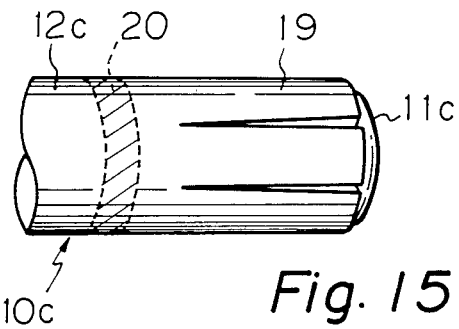
FIGS. 13, 14 and 15 are side elevational, end elevational and longitudinally sectional views, respectively, of the leading end portion of the endoscope according to the second embodiment of the present invention.
Figure 14:
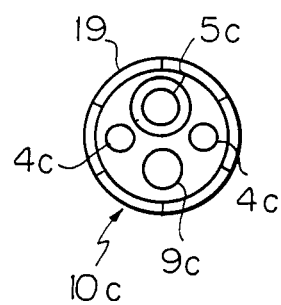
Figure 15:
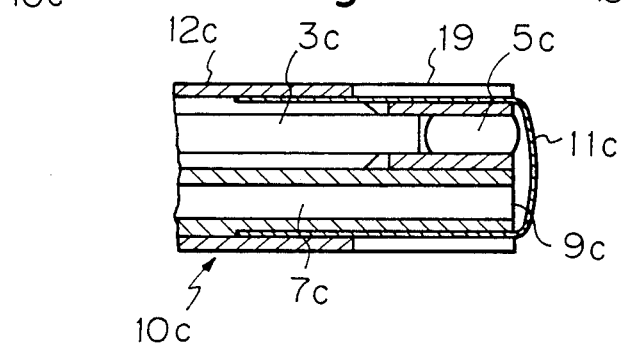
Figure 16:
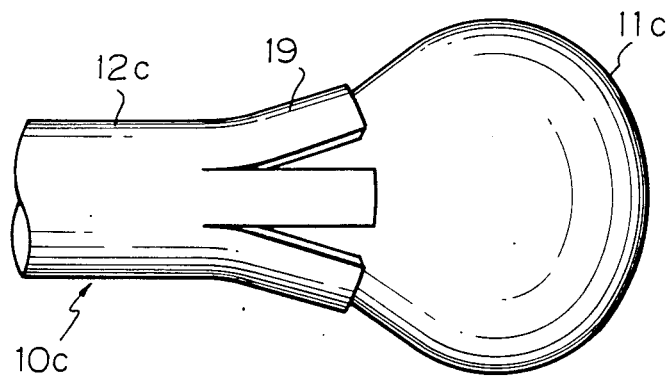
FIG. 16 is a view showing the inflated condition of the transparent balloon on the endoscope shown in FIG. 13.

FIGS. 13, 14 and 15 are side elevational, end elevational and longitudinally sectional views, respectively, of the second embodiment of the invention. The endoscope 10c of this second embodiment includes a substantially cylindrical, flexible and resilient balloon support. More specifically as shown in FIG. 13, the resilient leading end portion of the outer peripheral portion of the endoscope contiguous to a sheath 12c is substantially cylindrical and is divided into a plurality of resilient pieces 19 by a plurality of slits which extend axially and inwardly from the outer edge. The leading end portion of the outer periphery of the endoscope is formed of deformable synthetic resin such as polyethylene or vinyl chloride or metal such as phosphor bronze. In FIGS. 14 and 15, the same reference numerals, with the addition of sub-reference characters, denote the same components as those in the endoscope shown in FIGS. 3 and 4. The transparent balloon 11c is fitted in the sheath 12c and adhered to the sheath at the area 20. As more clearly shown in FIG. 16, when the balloon 11c is inflated, the resilient pieces 19 are subjected to the force resulting from the inflation of the balloon and deform radially outwardly from the bases to the outer ends of the resilient pieces in the form of a petal whereby the inflated balloon can be supported adjacent to the joint 20 over a wide range defined by the inner area of all the resilient pieces.

Figure 17:
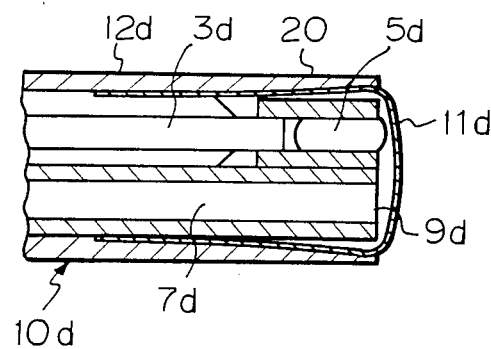
FIG. 17 is a longitudinally sectional view of the leading end portion of the endoscope according to the third embodiment of the present invention.
Figure 18:
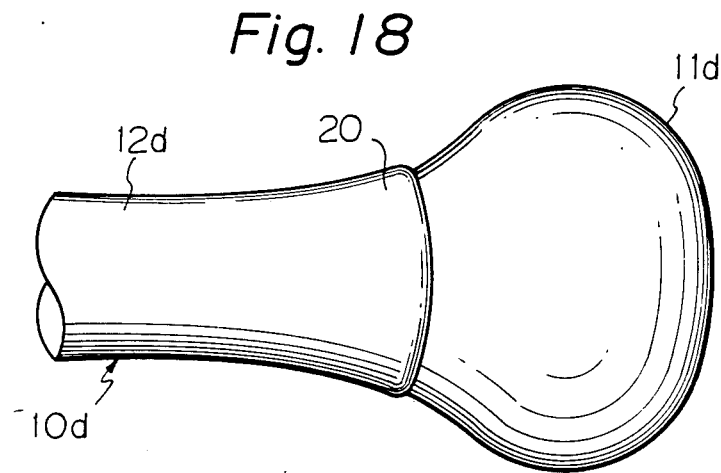
FIG. 18 is a view showing the inflated condition of the transparent balloon on the endoscope of FIG. 17.
Figure 19:
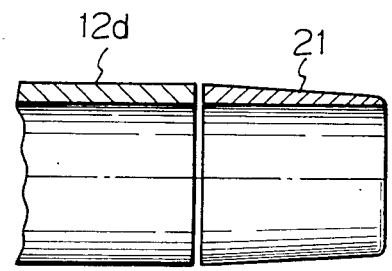
FIG. 19 is a view of a modification of the cylindrical portion in the embodiment shown in FIG. 17.

FIG. 17 is a longitudinally sectional view of the third embodiment of the invention. The endoscope 10d of this embodiment includes a substantially cylindrical, flexible and resilient balloon support 20 at the leading end portion of the endoscope. In FIG. 17, the same reference numerals, with addition of sub-reference characters, denote the same components as those in the embodiment shown in FIG. 15. Although, the end elevational view of the third embodiment is omitted, the light guide is arranged in the same manner as in the embodiment of FIG. 14. The leading end portion of the outer periphery of the endoscope which is contiguous to the sheath 12d is formed of extensible material such as natural rubber or urethane and provides the cylindrical support 20 which gradually decreases in wall thickness towards the leading edge. The balloon 11d is fitted in and adhered to the interior of the sheath 12d in the same manner as described in connection with the balloon shown in FIG. 13, but is not confined at the leading portion of the sheath due to a clearance formed by the gradual decrease in the wall thickness of the sheath. As more clearly shown in FIG. 18, when the balloon 11d is inflated, the inner periphery of the cylindrical support 20 is subjected to the force resulting from the inflation of the balloon and deforms to expand towards the leading end of the support whereby the transparent balloon can be supported adjacent to the joint thereof over a wide range defined by the inner area of the cylindrical support 20. The cylindrical support 20 may be in the form of a resilient cap 21, formed separately from the sheath 12d, as shown in FIG. 19.

With the above mentioned construction and arrangement of the components of the endoscope with a transparent balloon of the second and third embodiments, since the field of vision is formed by inflating the transparent balloon with the minimum amount of transparent fluid, the outer diameter of the endoscope can be made relatively small. Also, since the transparent balloon can be supported in stabilized condition adjacent to the joint thereof over a wide range by the flexible and resilient support, when the internal structure of a living body is observed by the use of the endoscope, the position of the inflated balloon will not readily change even when the balloon is subjected to variation in the extraction and feed pressure in the endoscope and/or the reaction force from the living body internal structure. Thus, a stable field of vision can be maintained during the observation operation. Furthermore, when the transparent balloon deflates, since the support formed of the flexible and resilient member returns from the expanded condition to the initial contracted condition, the endoscope can be inserted into the interior of a living body to be observed without difficulty.

Figure 20A:
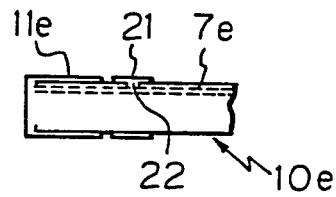
FIG. 20(a) shows the condition of the endoscope prior to inflation of the balloons thereof and FIG. 20(b) shows the condition of the endoscope after inflation of the balloons thereof.
Figure 20B:
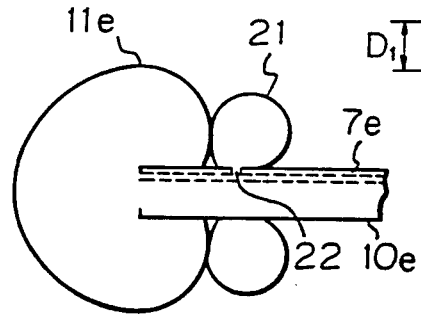
Figure 20C:
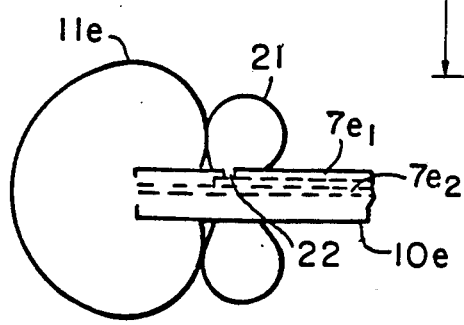
Figure 21A:
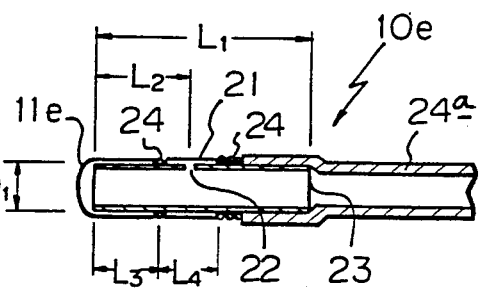
FIG. 21(a) is a view showing how to fabricate the endoscope and FIG. 21(b) is a view showing the endoscope after inflation of the two balloons thereof.

FIGS. 20 and 21 show the fourth embodiment of the present invention. The endoscope 10e of this embodiment includes a transparent balloon 11e at the leading end of the endoscope as a field of vision providing means and a support balloon 21 on the sheath 7e at the leading end portion of the endoscope behind the balloon 11e. FIG. 20(a) shows the balloons 11e, 21 in their position prior to inflation. In the illustrated embodiment, the balloon 11e is inflated by the transparent fluid from the leading end of the transparent fluid transport passage 7e and the support balloon 21 is inflated by a bypass fluid from a bypass hole 22 opened to the passage 7e.

FIG. 20(b) shows the balloons in their inflated position. The interiors of these balloons are maintained at the same pressure. In the inflated position of the balloons as shown in FIG. 20(b), the balloons 11e, 21 contact each other to prevent the transparent balloon from displacing. That is, the support balloon 21 supports the back side of the balloon 11e and prevents the balloon 11e from deforming when the balloons are inflated whereby the field of vision of the endoscope is maintained in a stable state.

It is preferable that separate fluid passages $7e_1$ and $7e_2$ are provided for the two balloons 11e, 21, respectively, as shown in FIG. 20(c). The internal pressure of the support balloon is preferably maintain higher than that of the transparent balloon to give a higher rigidity to the support balloon. The two balloons, and particularly the support balloon, are preferably formed of natural rubber or the like so that the balloons can be made as thin as possible and inflated to a substantial degree.

Figure 21B:
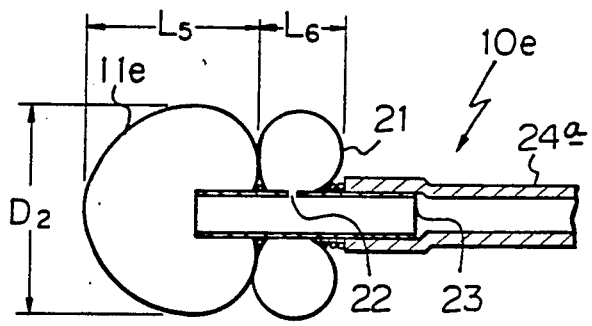

One specific example of this fourth embodiment will be now described below referring to FIG. 21. A natural rubber cap having the thickness of 0.03 mm is fitted on a stainless steel pipe 23 having an outer diameter of 2.7 mm and the cap is tied at the rear end and at an intermediate point of the cap by means of a string 24. The first balloon 11e is formed by the cap portion positioned forwardly of the intermediate tied point of the cap and the support balloon 21 is formed by the cap portion between the intermediate tied point and the tied rear end of the cap. A hole 22 of 0.5 mm diameter is formed in the wall of the pipe 23 at the area where the support balloon 21 is positioned. A syringe 24a is attached to the rear end of the pipe 23 and when air under pressure of about 0.3 kg/cm² is introduced into the assembly, the first and support balloons 11e, 21 are inflated as shown in FIG. 21(b). When the first balloon 11e is pressed against a suitable wall, it is apparent that the deformation of the first-mentioned balloon controlled by the support balloon is smaller than that of the transparent balloon of the conventional endoscope which has no support balloon. In FIG. 21, the other dimentions are as follows. $L_1=12$ mm, $L_2=6$ mm, $L_3=3.5$ mm, $L_4=4$ mm, $L_5=$about 10 mm, $L_6=$about 5 mm, $D_1=2.7$ mm and $D_2=$about 12 mm.

With the above mentioned construction and arrangement of the components of the endoscope of the fourth embodiment, the outer diameter of the endoscope can be made relatively small due to the same reasons stated in conjunction with the second and third embodiments. Also, in this fourth embodiment since the support balloon provides the same pushing effect as that which would be provided by a semi-rigid plate if such a plate were provided behind the first balloon to prevent the displacement of the deformation of the first balloon, the field of vision is made stable and the first balloon can be made as thin and transparent as possible.

Further, in this fourth embodiment, since a support member can be provided on the endoscope without substantially increasing the diameter of the latter, the endoscope can be quite easily inserted into the living body.

In the foregoing, although description has been made of the application of the endoscope of the invention to the observation of the internal structure of a living body, the endoscope can be also applied to a wide range of fields including various industrial and optical observation devices which provide a field of vision in an observation area filled with an opaque liquid.

What is claimed is:

1. An endoscope for image-observing or measuring an area filled with an opaque liquid comprising:
   an image fiber;
   a lens positioned at the leading end of said image fiber;
   a light guide arranged in parallel to said image fiber;
   a transparent fluid transport passage arranged in parallel to said image fiber and light guide and having an outlet at the leading end thereof;
   a sheath enclosing said image fiber, lens, light guide and transparent fluid transport passage;
   means for providing a field of vision at the leading end of said endoscope by a transparent fluid from said outlet of said transparent fluid transport passage; and
   stabilizing means provided on the leading end portion of said sheath for stabilizing said field of vision formed by said field of vision providing means
   said field of vision providing means including a transparent balloon provided at the leading end of said endoscope encircling said lens, the leading end of said light guide and the outlet of said transparent fluid transport passage and being inflatable by the transparent fluid from said opening;
   said stabilizing means including a substantially cylindrical balloon support means formed of a resilient material and provided at the leading end of said endoscope so as to encircle the joint portion of said balloon, said balloon support means in response to inflation of said balloon, being gradually expanded in a direction from a trailing end toward a leading end thereof for supporting the balloon joint portion when said balloon is inflated.

2. An endoscope as set forth in claim 1, in which said balloon support means is formed of resin and is divided into a plurality of pieces by a plurality of slits which extend axially and inwardly from an outer edge, of said balloon support means.

3. An endoscope as set forth in claim 2, in which said resin is polyethylene or vinyl chloride.

4. An endoscope as set forth in claim 1, in which said balloon support means is formed of a metal cylinder contiguous with the leading end of said sheath and is divided into a plurality of pieces by a plurality of slits which extend axially and inwardly from an outer edge of said balloon support means.

5. An endoscope as set forth in claim 4, in which said metal cylinder is formed of phosphor-bronze.

6. An endoscope as set forth in claim 1, in which said balloon support is a cylinder formed of extensible material which gradually decreases in thickness in the axial direction towards the leading end of the cylinder and is disposed at the leading end of said sheath.

7. An endoscope as set forth in claim 6, in which said extensible material is natural rubber or urethane.

8. An endoscope as set forth in claim 6, in which said cylinder is axially contiguous with said sheath and integral therewith.

9. An endoscope as set forth in claim 6, in which said cylinder is a resilient cap separate from said sheath and is axially aligned therewith.

10. An endoscope for image-observing or measuring an area filed with an opaque liquid comprising:
    an image fiber;
    a lens positioned at the leading end of said image fiber;
    a light guide arranged in parallel to said image fiber;
    a transparent fluid transport passage arranged in parallel to said image fiber and light guide and having an outlet at the leading end thereof;
    sheath enclosing said image fiber, lens, light guide and transparent fluid transport passage;
    means for providing a field of vision at the leading end of said endoscope by a transparent fluid from said outlet of said transparent fluid transport passage; and
    stabilizing means for stabilizing said field of vision formed by said field of vision providing means,
    said field of vision providing means including a transparent balloon provided at the leading end of said endoscope encircling said lens, the leading end of said light guide and the outlet of said transparent fluid transport passage and being inflatable by the transparent fluid from said opening, and
    said stabilizing means including a support balloon mounted on said sheath behind said transparent balloon for supporting a backside of the transparent balloon when said transparent and support balloons are inflated to thereby limit the sway of the transparent balloon during observation operation.

11. The endoscope as set forth in claim 10, in which a rubber cap is fitted on said sheath at the leading end portion of said endoscope, said rubber cap is tied at the rear end and at an intermediate point thereof to said sheath whereby said transparent balloon is formed by the cap portion positioned forwardly of said tied intermediate point and said support balloon is formed by the cap portion between said tied intermetiate point and the tied rear end.

12. An endoscope as in claim 10 wherein said fluid transparent passage includes first and second fluid transport passages respectively communicating with said transparent balloon and said support balloon.

13. An endoscope for image-observing or measuring an area filled with an opaque liquid comprising:
   an image fiber;
   a lens positioned at the leading end of said image fiber;
   a light guide arranged in parallel to said image fiber;
   a transparent fluid transport passage arranged in parallel to said image fiber and light guide and having an outlet at the leading end thereof;
   a sheath enclosing said image fiber, lens, light guide and transparent fluid transport passage;
   means for providing a field of vision at the leading end of said endoscope by a transparent fluid from said outlet of said transparent fluid transport passage; and
   stabilizing means provided on the leading end portion of said sheath for stabilizing said field of vision formed by said field of vision providing means,
   said field of vision providing means being provided by a flush of the transparent fluid directly exiting from said outlet of said transparent fluid transport passage into said opaque liquid, and
   said stabilizing means including an expandable hood surrounding said lens, the leading end of said light guide, the opening of said transparent fluid transport passage and said flush of the transparent fluid.

14. An endoscope as set forth in claim 13, in which said hood forms an extension of said sheath at the leading end of said endoscope.

15. An endoscope as set forth in claim 13, in which said hood is formed of a resilient material and includes a balloon device in the wall of said hood.

16. An endoscope as set forth in claim 15, in which said resilient material is rubber.

17. An endoscope as set forth in any one of claims 1 to 16, in which said opaque liquid is blood and said endoscope is one used for observing a blood vessel or the internal wall of the heart of a living body.

* * * * *